United States Patent [19]
Milo

[11] Patent Number: 5,102,625
[45] Date of Patent: Apr. 7, 1992

[54] APPARATUS FOR MONITORING A CHEMICAL CONCENTRATION

[75] Inventor: Charles Milo, Agoura Hills, Calif.

[73] Assignee: BOC Health Care, Inc., Murray Hill, N.J.

[21] Appl. No.: 480,995

[22] Filed: Feb. 16, 1990

[51] Int. Cl.$^5$ .............................................. G01N 21/61
[52] U.S. Cl. ............................... 422/82.07; 422/82.06; 422/52; 422/86; 250/227.21; 250/458.1; 250/461.1; 436/172; 385/123
[58] Field of Search ................. 350/96.29; 250/227.21, 250/458.1, 461.1, 227.23; 436/136, 127, 172; 422/52, 82.07, 82.06, 86

[56] References Cited

U.S. PATENT DOCUMENTS

| | | |
|---|---|---|
| 3,999,099 | 12/1976 | Herion . |
| 4,305,641 | 12/1981 | Witte et al. . |
| 4,321,057 | 3/1982 | Buckles . |
| 4,476,870 | 10/1984 | Peterson et al. . |
| 4,498,004 | 2/1985 | Adolfsson et al. ............. 250/227.23 |
| 4,542,104 | 9/1985 | Stryer et al. ........................ 436/537 |
| 4,576,173 | 3/1986 | Parker et al. . |
| 4,592,361 | 6/1986 | Parker et al. . |
| 4,657,736 | 4/1987 | Marsoner et al. . |
| 4,712,865 | 12/1987 | Hsu et al. . |
| 4,725,128 | 2/1988 | Bornzin et al. . |
| 4,752,115 | 6/1988 | Murray, Jr. et al. . |
| 4,775,514 | 10/1988 | Barnikol et al. ..................... 436/136 |
| 4,810,655 | 3/1989 | Khalil et al. .......................... 128/633 |
| 4,861,727 | 8/1989 | Hauenstein et al. ................. 436/136 |
| 4,880,972 | 11/1989 | Brogardh et al. .............. 250/227.23 |
| 4,900,933 | 2/1990 | Nestor et al. ..................... 250/458.1 |
| 4,900,934 | 2/1990 | Peeters et al. .................... 250/461.1 |
| 4,925,268 | 5/1990 | Iyer et al. ......................... 350/96.29 |
| 5,001,338 | 3/1991 | Boero ............................. 250/227.21 |

FOREIGN PATENT DOCUMENTS

| | | |
|---|---|---|
| 0252578 | 1/1988 | European Pat. Off. . |
| 0283289 | 9/1988 | European Pat. Off. . |
| 2132348 | 6/1984 | United Kingdom . |
| 87/00023 | 1/1987 | World Int. Prop. O. . |

OTHER PUBLICATIONS

Zhujun et al., "A Fluorescence Sensor for Quantifying pH in the Range from 6.5 to 8.5", analytica Chimica Acta 160 (1984), 47–55.

Scheggi et al., "pH Sensing by Fiber Optics", Optica Acta 1986, vol. 33, No. 1587–1597.

Wolfbeis et al., Fluorimetric Analyses: A Study on Fluorescence Indicators for Measuring Near Neutral ("Physiological") pH Values, Fresenius Z Anal Chem. (1983) 314: 119–124.

*Primary Examiner*—David L. Lacey
*Assistant Examiner*—N. Edwards
*Attorney, Agent, or Firm*—Roger M. Rathbun; Larry R. Cassett

[57] ABSTRACT

A sensor for monitoring a condition such as a chemical concentration includes two luminescent materials having differing absorption bands and differing sensitivities to the condition to be monitored. Light in the two absorption bands is applied in alternating sequence so as to elicit emissions from the two luminescent materials in alternating sequence. These emissions are compared to one another and the relationship between them, such as the ratio of their intensities, indicates the condition. The luminescent materials may be porphyrins or derivatives thereof.

23 Claims, 3 Drawing Sheets

APPARATUS FOR MONITORING A CHEMICAL CONCENTRATION

BACKGROUND OF THE INVENTION

The present invention relates to apparatus and methods for monitoring a condition such as a chemical concentration of an analyte by monitoring the effect of the condition on a luminescent material.

It has long been recognized that the emission of light by certain luminescent materials is affected by conditions prevailing in the vicinity of the luminescent material. For example, the intensity or lifetime of light emissions from certain luminescent materials are affected by chemical conditions such as the partial pressure of oxygen ("$PO_2$") surrounding the material. Various attempts have been made to use this effect in instruments for monitoring chemical conditions. Ordinarily, such instruments include a luminescent material and appropriate devices for applying excitation light to the luminescent material thereby provoking emission of response light from the luminescent material. The apparatus is arranged to expose the luminescent material to a sample so that the emission may be affected by a chemical condition prevailing within the sample, and to monitor one or more properties of the light emitted by the luminescent material, which properties vary with the condition to be measured. Thus, Khalil et al, U.S. Pat. No. 4,810,655 discloses an instrument for measuring the time dependence of phosphorescence from a phosphorescent material disposed at the end of a fiber optic while the fiber optic is inserted in the sample. The sample may be the blood within a living subject. European Patent Application No. 0,252,578 discloses a similar device for monitoring the time dependence of fluorescence emissions. Although measurement of the decay time characteristics can provide useful information, such measurements generally require rather complex electronics and, hence, do not lend themselves to implementation in a simple and economical instrument.

Parker et al, U.S. Pat. Nos. 4,592,361 and 4,576,173 disclose an apparatus for monitoring the intensity or amplitude of emission from a phosphorescent material in admixture with the tissue of a living subject. These instruments employ various measures to separate the desired long lived phosphorescence emission which is representative of the singlet oxygen content of the tissue from unwanted interfering emissions. Peterson et al, U.S. Pat. No. 4,476,870 discloses an instrument for monitoring oxygen concentration in a living subject by directing excitation light onto a phosphorescent material in contact with the subject and detecting both scattered excitation light and phosphorescence light emitted by the sample. The instrument is arranged to determine the ratio between the scattered excitation light and the phosphorescent light, which ratio serves as a measure of the phosphorescence quenching by oxygen. Such an instrument depends on the stability of the phosphorescent material. Changes in the response characteristics of the phosphorescent material would change the results obtained.

British Published Patent Application No. 2,132,348A discloses a sensor for visual observation. An oxygen-sensitive luminescent material is mounted in a film or layer of an oxygen permeable polymer. A reference luminescent material substantially insensitive to oxygen is mounted adjacent the oxygen-sensitive luminescent material so that the luminescent responses of the two materials can be compared visually, so as to provide a crude measure of oxygen concentration prevailing in the vicinity of the luminescent materials.

European Patent Application No. 0,283,289 discloses an instrument which employs two luminescent materials having different sensitivities to the condition to be sensed. Both luminescent materials are excited into luminescence by excitation light at 350–400 nm wavelength, in the ultraviolet region of the spectrum. The response light from the two luminescent materials is at different wavelengths and is separated by filtering through optical bandpass filters. The ratio of response light amplitudes is determined as a measure of the condition to be monitored.

Despite all of these efforts towards development of luminescence-based instruments for monitoring chemical conditions, there are still significant chemical needs for further improvements.

SUMMARY OF THE INVENTION

The present invention addresses these needs.

One aspect of the present invention provides apparatus for monitoring a condition such as a chemical concentration or other chemical condition. The apparatus includes a probe having first and second luminescent materials. The probe also includes means for exposing the luminescent materials to the condition to be monitored. The first luminescent material is adapted to absorb light within a first band of absorption wavelengths and to temporarily emit light in response to such absorption. The second luminescent material is adapted to absorb light in a second band of absorption wavelengths and to temporarily emit light in response to such absorption. At least a portion of the second absorption band desirably is outside of the first absorption band. There is a relationship between the intensity of light emission from the first luminescent material and the condition to be monitored and a further relationship between the intensity of light emission from the second luminescent material and the condition to be monitored. These relationships are different from one another. Stated another way, the luminescent materials have different sensitivities to the condition to be monitored. For example, in an apparatus intended to monitor oxygen concentration in a sample, the first luminescent material may be an oxygen-sensitive luminescent material having emission intensity which varies substantially with oxygen concentration, whereas the second luminescent material may be substantially insensitive to oxygen, so that the emission intensity is substantially constant for varying oxygen concentrations.

The apparatus desirably also includes means for applying first excitation light at one or more wavelengths within the first absorption band but outside the second absorption band, and second excitation light at one or more wavelengths within the second absorption band but outside the first absorption band to the luminescent materials in the probe. Desirably, the means for applying excitation light is arranged to apply the first and second excitation light alternately so that the luminescent materials in the probe will emit response light in an alternating sequence including first response intervals of emission by the first luminescent material and second response intervals of emission by the second luminescent material. The apparatus preferably further includes means for detecting the response light emitted by the luminescent materials and providing a first signal representing the magnitude of the response light during the first response intervals and a second signal representing the magnitude of the response light during the second response intervals. Thus, the first and second signals will represent the intensity of emission by the first and second luminescent materials respectively. The apparatus preferably further includes means responsive to the first and second signals for determining a quantitative relationship between the magnitudes represented by the signals. Because the emission intensity from the first luminescent material bears a different relationship to the condition to be monitored than does the emission intensity from the second luminescent material, the quantitative relationship derived in response to the first and second signals will vary in accordance with the condition to be monitored.

Desirably, the first and second luminescent materials have substantially equal susceptibility to loss or change in their emission intensity upon exposure to the excitation light. Thus, many luminescent materials are susceptible to a phenomenon known as "bleaching," wherein the luminescent materials gradually decay into inactive forms when exposed to light within their respective absorption bands. Where both luminescent materials are susceptible to such bleaching, the bleaching does not substantially change in the relationship between their respective emission intensities and hence does not substantially affect the measurement obtained by the apparatus. Likewise, the relationship between the respective emission intensities as measured by the instrument will be substantially unaffected by changes in the optical components of the apparatus. For example, where the probe incorporates a fiber optic, changes in the physical configuration of the fiber optic which might affect its light transmissivity will affect light emitted by both luminescent materials equally and hence will not alter the relationship between their respective emission intensities.

The preferred apparatus according to this aspect of the present invention can measure the relationship between the emissions from the luminescent materials using relatively simple electronic circuitry. Thus, because the emissions occur at different intervals in the repeating sequence, there is no need for complex electronics to separate the signals representing the luminescence from the two materials. The apparatus may include a simple arrangement of light sources and an appropriate timing circuit for providing the alternating excitation light and one or more photodetectors for providing electrical signals representative of the response light, together with a simple switching arrangement activated by the timing circuit for delivering the signals from the photodetectors during appropriate portions of the alternating response light sequence. Thus, the signal from the photodetector or photodetectors can be routed along one circuit during first response intervals and along another circuit during the second response intervals so that the signals on the first and second circuits will constitute the first and second signals representing the emission intensities of the first and second luminescent materials, respectively. Once the emission intensity signals have been separated by such simple timing and switching elements, the quantitative relationship between them can be determined by well-known signal comparison devices such as analog or digital dividing circuits. Thus, the entire instrument can be simple and economical.

According to a further aspect of the invention, the luminescent materials are selected so that their respective absorption bands lie substantially within the range of visible light wavelengths, and so that the luminescent materials emit response light which is also at visible wavelengths. The probe may include a polymeric member substantially transparent to visible light in the absorption bands and substantially transparent to the visible response light emitted by the luminescent materials. The means for applying excitation light to the luminescent materials of the probe may include means for directing the excitation light to the luminescent materials through the polymeric member, whereas the means for detecting response light may include means for detecting response light through the polymeric member. The polymeric member may be a polymeric fiber optic. Most preferably, the luminescent materials in the probe according to this aspect of the present invention are selected from the group of porphyrin class compounds further defined below. In the preferred probes according to this aspect of the present invention, the ability to use visible light for observation of the luminescent material permits use of an economical polymeric members such as polymeric fibers. By contrast, many of the luminescence-based sensors utilized heretofore have required transmission of ultraviolet light to or from the luminescent material. As polymers tend to absorb ultraviolet light, such instruments typically have required costly and delicate glass light transmissive members. In the preferred sensor according to the present invention, the combination of the porphyrin class luminescent materials and a polymeric fiber provides an efficient and economical probe. In particular, the preferred probes according to this aspect of the present invention can be so economical that the same may be discarded after a single use. This is of particular importance in biomedical applications.

Further aspects of the present invention provide methods of monitoring a condition such as a chemical condition. Most preferably, methods according to this aspect of the present invention utilize luminescent materials having different absorption bands, and include the steps of supplying the excitation light in two different absorption bands in alternating sequence as discussed above, monitoring the emitted response light, and segregating the signals representing emission of the two luminescent materials by timing as noted above in connection with the apparatus. Most preferably, the luminescent materials utilized in a method according to this aspect of the invention are porphyrin-class materials, and the light is transmitted to and from the luminescent materials via a polymeric light-transmissive member such as an optical fiber.

These and other objects, features, and advantages of the present invention will be more readily apparent from the detailed description of the preferred embodiments set forth below, taken in conjunction with the accompanying drawings.

DETAILED DESCRIPTION OF THE PREFERRED EMBODIMENTS

Figure 1:
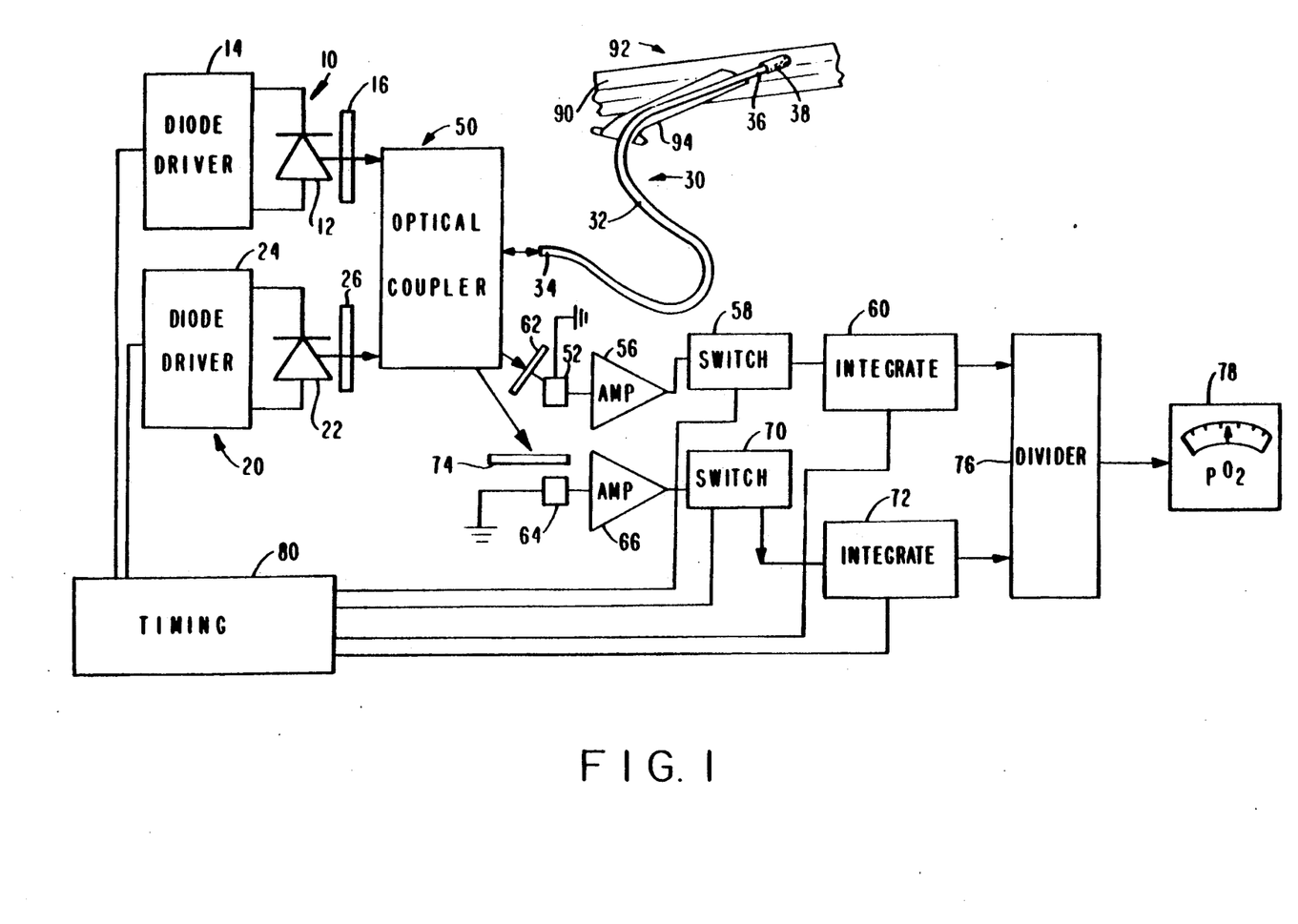
FIG. 1 is a schematic view, partially in block diagram form, of apparatus in accordance with an embodiment of the present invention.
Figure 2:
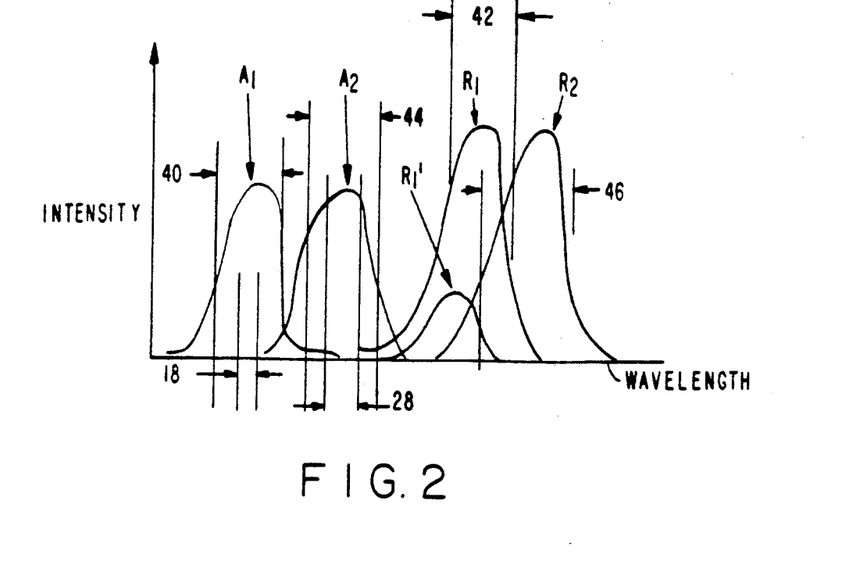
FIG. 2 is an idealized graph depicting the absorption and emission spectra of certain luminescent materials utilized in the apparatus of FIG. 1.

Apparatus in accordance with one embodiment of the present invention incorporates a first excitation light source 10 including a light emitting diode 12 and a diode driver or power supply 14, together with an optical band pass filter 16. Driver 14 is arranged to momentarily actuate diode 12 upon receipt of a control signal. Band pass filter 16 is arranged to limit the light emitted by diode 12 to only a predetermined range of first excitation wavelengths 18 (FIG. 2). The apparatus also includes a second excitation light source 20 including a similar diode 22 and diode driver 24, together with an optical band pass filter 26. Filter 26 is arranged to limit the light emitted by the second source to a different band of wavelengths 28 (FIG. 2).

The apparatus also includes a probe 30 incorporating a polymeric optical fiber 32 having a proximal end 34 and a distal end 36. Fiber 32 desirably is formed from a polymer which is transparent to light in the visible range, such as a polymer selected from the group consisting of acrylic polymers, polystyrene, and polymethyl methacrylate or else may be a glass optical fiber. Where the instrument is intended for use in biomedical application, as for insertion into the vascular system of a mammalian organism, the fiber optic 32 desirably is less than about 450 micrometers in diameter, and more preferably about 140 micrometers in diameter or less. A mass 38 of a luminescent composition is mounted to the distal end 36 of the fiber. Luminescent composition 38 incorporates first and second luminescent materials in a transparent, oxygen permeable polymeric binder. Suitable polymers for use as a binder include those selected from the group consisting of substituted and unsubstituted polysiloxanes; copolymers and blends of substituted and unsubstituted siloxanes with polycarbonates and polystyrenes, such as block copolymers of a siloxane and bis-phenol A and block copolymers of a siloxane with alphamethylstyrene; and polyurethanes. Combinations of these materials may also be employed.

The first luminescent material is arranged to absorb light within a predetermined absorption band and to temporarily emit light responsive to such absorption. Most preferably, the first luminescent material is adapted to emit light by phosphorescence, so that the emission continues for an appreciable period, desirably about one millisecond to about 10 seconds, after the absorption ends. The emission wavelengths are longer wavelengths than the absorbed wavelengths. Thus, the first luminescent material may have an absorption and emission spectrum as indicated schematically in FIG. 2, the absorptivity of the material being indicated by curve $A_1$ and the response or emission spectrum being indicated by curve $R_1$. Thus, the first luminescent material is adapted to substantially absorb light only within a first band 40 of absorption wavelengths. As will be appreciated, the first luminescent material may have some minor absorptivity for light outside of band 40 and the curve of absorptivity versus wavelength may decrease gradually adjacent the borders of band 40. However, for purposes of this disclosure, the practical limits of absorption band 40 may be taken as the wavelengths where the absorptivity of the first luminescent material is about 5% of the maximum absorptivity. Likewise, as illustrated by curve $R_1$, the first luminescent material is arranged to emit light, responsive to absorption in band 40, in a predetermined response wavelength band 42. For purposes of this disclosure, the response wavelength band may be taken as the band of wavelengths encompassing a peak emission intensity and extending above and below the peak wavelength to a wavelength where the emission intensity is about 5% of the emission intensity at the peak wavelength. The first luminescent material is substantially sensitive to oxygen. Thus, curve $R_1$ shows the emission spectrum in the absence of oxygen. In the presence of oxygen, the emission within band 42 is substantially diminished. The emission spectrum is still centered on the same peak wavelength, but the peak intensity of emission for a given amount of incident light incident on the luminescent material is lower, as indicated by curve $R'_1$. Where there is a small amount of oxygen present, the emission spectrum of the first luminescent material will be intermediate between curves $R_1$ and $R'_1$. The reduction of emission may be caused by reduction of the absorptivity within band 40, or by quenching of the emission, or both.

The second luminescent material has absorption and emission curves $A_2$ and $R_2$, respectively. The second luminescent material is adapted to absorb the light in a predetermined second band of absorption wavelengths 44 and to emit light in a second band of emission wavelengths 46. As seen in FIG. 2, at least some, and preferably all of the second band 44 of absorption wavelengths lies outside of the first band 40 of absorption wavelengths. The emission bands 42 and 46 may overlap in whole or in part. The absorption and emission bands of both luminescent materials are within the visible light spectrum and hence within the range of wavelengths transmissible through fiber 32. The emission intensity from the second luminescent material is substantially insensitive to oxygen. Thus, provided that all other conditions are maintained constant, the emission intensity from the second luminescent material in band 46 will be substantially constant regardless of oxygen concentration. Thus, the relationship between emission intensity and oxygen concentration for the first luminescent material is different from the relationship between oxygen concentration and luminescent emission intensity for the second luminescent material.

Most preferably, the luminescent materials are porphyrin-class compounds. The luminescent materials may be selected from the group consisting of porphyrin; chlorin; bacteriochlorin; isobacteriochlorin; porphyrinogen; and derivatives thereof. Most preferably, the luminescent materials are selected from the group consisting the aforementioned named compounds, alkyl- and aryl-substituted derivatives of the aforementioned named compounds, and the metallo derivatives of the named compounds and their alkyl- and aryl-substituted derivatives. Thus, the preferred luminescent materials include compounds according to any of the following structural formulae:

porphyrin chlorin bacteriochlorin isobacteriochlorin

-continued porphyrinogen wherein $R_1$ through $R_{12}$ are the same or different and are selected from the group consisting of hydrogen, substituted and unsubstituted aryl moieties, and substituted and unsubstituted alkyl moieties. Compounds according to all of these formulae are commonly referred to as "free base porphyrins". The preferred luminescent materials further include the metallo derivatives of compounds according to the aforementioned structural formulae. In the metallo derivatives, two of the hydrogen atoms shown as bound to the nitrogen moieties adjacent the center of each ring are omitted, and a metallic moiety is bound to the nitrogen moieties adjacent the center of each structure. The metallo derivatives may have either a metal moiety per se or a complex moiety incorporating a metal, such as a metal carbonyl moiety bound to the nitrogen moieties of the basic ring structure in place of the hydrogen moieties. In a particularly preferred subclass of these materials, $R_5$ through $R_{12}$ are all hydrogen, whereas each of $R_1$ through $R_4$ is an aryl moiety, most preferably a phenyl moiety. In another preferred subclass of luminescent materials, each of $R_1$ through $R_4$ is hydrogen, whereas each of $R_5$ through $R_{12}$ is an alkyl moiety, most preferably an unsubstituted ethyl moiety.

In general, the platinum and palladium metallo derivatives of these materials are susceptible to quenching by oxygen, whereas the metallo derivatives other than platinum or palladium, and the non-metallo derivatives are substantially insensitive to oxygen. Thus, zinc, nickel, copper, and cobalt metallo derivatives, and ruthenium carbonyl derivatives of the aforementioned materials are substantially insensitive to oxygen quenching.

The apparatus also includes a conventional optical coupler 50 arranged to connect the first and second excitation light sources 10 and 20 to the proximal end 34 of fiber 32, so that excitation light emitted by the light sources will be transmitted through the fiber to the mass 38 of luminescent composition. As best appreciated with reference to FIG. 2, the pass band 18 of the optical filter 16 in the first excitation light source 10 is selected so that it lies within the absorption band 40 of the first luminescent material and outside of the absorption band 44 of the second luminescent material. The pass band 28 of optical filter 26 in the second excitation light source 20 lies within the absorption band 44 of the second luminescent material but outside of the absorption band 18 of the first luminescent material. As used in this disclosure with reference to an optical filter, the term "pass band" refers to a range of wavelengths which can be transmitted through the filter.

The apparatus further includes a first photodetector 52 connected to the input of an amplifier 56. Photodetector 52 may be a conventional photomultiplier tube. The output of amplifier 56 is electrically connected by a conventional solid state semiconductor switch 58 to the input of an integrator 60. The first photodetector 52 is optically connected via an optical band pass filter 62 and coupler 50 to the proximal end 34 of fiber 32. The pass band of filter 62 is selected so that it encompasses a range of wavelengths within the emission wavelength band 42 of the first luminescent material. Thus, response light emitted by the first luminescent material within band 42 will be directed onto photodetector 52. A second photodetector 64 is connected to a similar amplifier 66, switch 70, and integrator 72. Second photodetector 64 is optically connected through a second optical band pass filter 74 and through coupler 50 to the proximal end 34 of fiber 32. The pass band of filter 74 is selected so that it encompasses wavelengths within the second emission band 46 of the second luminescent material in composition 38. In this regard, it is permissible for the pass bands of filters 62 and 74 to overlap one another. These filters are not required to discriminate between emissions from the first and second luminescent materials, but rather simply to reduce stray light and noise. Desirably, the pass bands of filters 62 and 74 do not substantially overlap the pass bands of filters 16 and 26, so that the filters 62 and 74 of the photodetectors will effectively screen out excitation light and will protect the photodetectors 52 and 64 from overloading as might be occasioned by exposure to excitation light.

The outputs of integrators 60 and 72 are connected to an analog dividing circuit 76 arranged to divide the output from integrator 72 by the output from integrator 60, and hence to compute a ratio between the magnitudes of the signals output by the integrators. The output of divider 76 is connected to a meter 78 or other suitable device for producing a perceptible indication of the signals output by divider 76. Thus, meter 78 could be replaced by a chart recorder, digital readout, or other suitable output device. Alternatively, the output from divider 76 may be connected to a suitable recording device so that the output can be recorded rather than immediately displayed. As another alternative, the output from divider 76 can be connected as a control input to other apparatus which is to be controlled in response to the condition monitored by the apparatus according to the invention.

A timing device 80 is connected to diode drivers 14 and 24 and to switches 58 and 70. The timing device 80 may be a conventional multi-channel programmable timer arranged to provide actuation signals in a predetermined sequence. Thus, electromechanical and mechanical timing devices may be employed, although fully electronic timing devices are greatly preferred.

In a method according to one embodiment of the invention, the mass 38 of luminescent composition is contacted with a sample in which the oxygen concentration is to be monitored. As shown in FIG. 1, the sample may be the blood within a blood vessel 90 of a human or other mammalian organism 92 and the mass 38 of luminescent material may be positioned within the blood vessel by advancing the distal end 36 of fiber 32 into the blood vessel through a conventional intravascular access device such as a conventional intravascular catheter 94.

Figure 3:
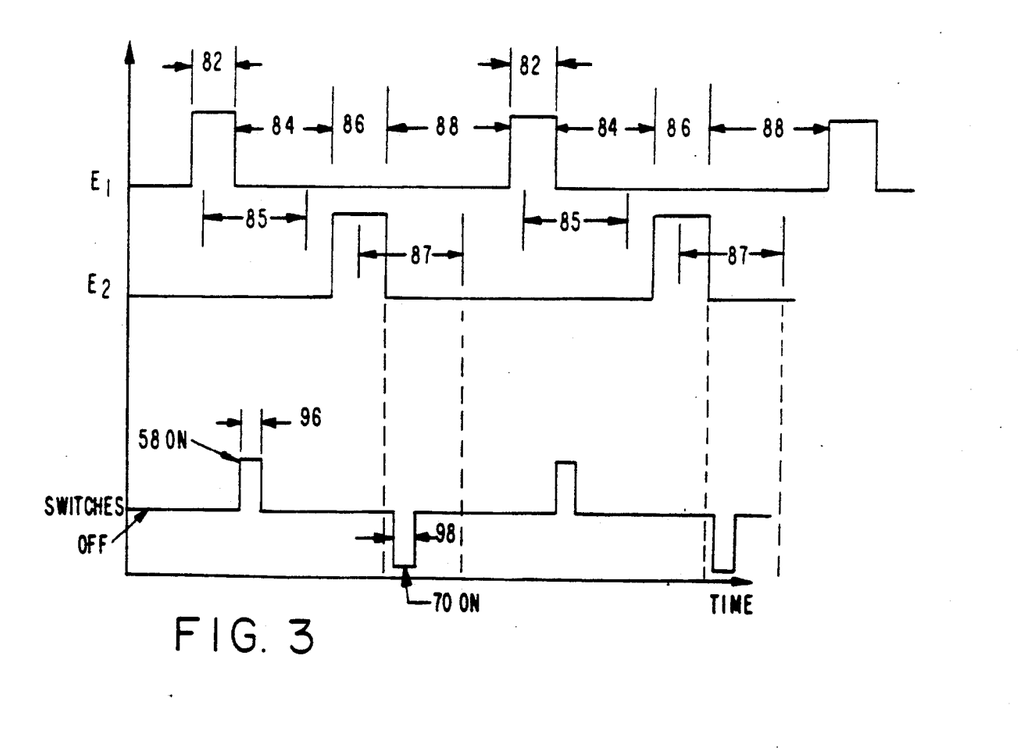
FIG. 3 is a graph depicting the timing of certain steps in operation of the apparatus of FIG. 1.

Timing device 80 is arranged to provide actuation signals to diode drivers 14 and 24 in alternating sequence, so that the first light source 10 and second light source 20 are actuated alternately, with delay or dwell times between the termination of actuation of one light source and the beginning of actuation of the next light source. This pattern of actuation is schematically indicated in FIG. 3, wherein curves $E_1$ and $E_2$ represent the actuation of the first and second light sources 10 and 20, respectively. As illustrated, first light source 10 is actuated during a first illumination interval 82, which is followed by a dwell period 84 during which neither light source is actuated. A second illumination interval 86 during which the second light source 20 is actuated follows immediately after dwell period 84, and a second dwell period 88 during which neither light source is actuated follows immediately after second actuation period 86. This same sequence repeats over and over again.

Timing apparatus 80 also actuates switches 58 and 70 in alternating sequence so that switch 58 is closed or turned on only during preselected first sampling intervals 96 and switch 70 is closed or turned on only during preselected intervals 98, the switches being off or nonconductive at other times. The timing of the sampling intervals 96 and 98 is coordinated with the timing of the excitation light intervals 82 and 36 so that each first sampling interval 96 falls during a first source illumination interval 82. Likewise, each second sampling interval 98 falls within a second source illumination interval 86.

The excitation light from the first light source 10 applied during each interval 82 falls within the absorption band 40 of the first luminescent material but outside the absorption band 44 of the second luminescent material. Therefore, the excitation light applied during first illumination intervals 82 will cause the first luminescent material to begin emitting response light. Such emission will continue at a substantially constant or "steady state" value during the latter portion of each first illumination interval 82. The response light will decay gradually, during the immediately succeeding dwell interval 84. Thus, the first luminescent material emits response light during first response intervals 85, each such interval beginning during a first illumination interval 82 and continuing into the succeeding dwell period 84. The duration of each dwell period 84 is selected so that the response light emission from the first luminescent material is substantially completely decayed by the beginning of the next succeeding second illumination interval 86.

During each second illumination interval 86, the excitation light is applied only by second light source 20. This excitation light is applied in absorption band 44 of the second luminescent material but outside of the absorption band 40 of the first luminescent material. Therefore, the excitation light applied during each second illumination interval 86 will cause the second luminescent material to emit response light. Such emission will continue at a substantially constant or steady state value, and then will decay progressively during the next succeeding dwell interval 88. Here, again, the timing is selected so that the luminescence from the second luminescent material has substantially decayed by the next first illumination interval 82. Thus, the second luminescent material emits response light during second response intervals 87, each commencing during a second illumination interval 86 and continuing into the next dwell period 88.

During each first response interval 85 the response light emitted by the luminescent materials in mass 38 consists essentially of response light emitted by the first luminescent material. Accordingly, the signal provided by photodetector 52 and amplifier 56 during each first response interval 85 will be an analog signal representing the emission intensity of the first luminescent material only. Switch 58 is actuated only during first sampling intervals 96, which lie within the steady state or constant response portions of first response intervals 85. Thus, only the analog signal representing the steady state emissions from the first luminescent material is routed to integrator 60. During other intervals, such as during second response intervals 87, the analog signal from first photodetector 52 and first amplifier 58 may incorporate a spurious component caused by emissions from the second luminescent material. However, because switch 58 is off or non-conducting during such other intervals, this spurious component does not pass to integrator 60. Likewise, the signal from second photodetector 64 and second amplifier 66 consists essentially of a signal representing steady state emissions from the second luminescent material during each second response interval 87, and this signal is routed to integrator 72 during each second sampling interval 98, when switch 70 is turned on. Again, during other intervals, a signal from the second photodetector and second amplifier 66 may incorporate other components, but switch 70 is turned off during such other intervals. Therefore, the signal passing to integrator 72 is a signal representing essentially only the steady state emissions from the second luminescent material.

Integrator 60 integrates all of the signals received during succeeding first sampling intervals 96 so as to provide an average value for all of these signals. This average value is proportional to the magnitude of each analog signal received by the integrator received during each interval 96 and hence proportional to the magnitude of the emissions from the first luminescent material during the various intervals 96. Likewise, integrator 72 averages the magnitudes of the analog signals received during the intervals 98, and hence provides an average value for the magnitude of emissions from the second luminescent material. Divider circuit 76 divides the average value from integrator 72 by the average value delivered by integrator 60. The divider thus provides an output signal representing the ratio of the average value from integrator 72 to the average value from integrator 60. This ratio represents the ratio between the analog signal delivered by the first photodetector 52 during each interval 96 to the average value of the signal delivered by the second photodetector 64 during each interval 98. The ratio thus represents the ratio between the steady state luminescent emission intensity of the second luminescent material and the steady state luminescent emission intensity of the first luminescent material. This ratio or relationship will charge according to the oxygen concentration prevailing at mass 38 and hence according to the $PO_2$ of the blood in vessel 90. As discussed above, the intensity of emissions from the first luminescent material varies inversely with oxygen concentration, whereas the emission intensity from the second luminescent material does not vary substantially with oxygen concentration. Therefore, as oxygen concentration increases, the ratio of second material intensity to first material intensity will also increase. The ratio thus varies directly with oxygen concentration. This ratio, as derived by divider circuit 76, is displayed directly on meter 78. Timing unit 80 periodically resets integrators 60 and 72 to zero, so as to begin a new integration cycle, and derive a new value of $PO_2$.

As will be appreciated, numerous variations and combinations of the features discussed above can be utilized without departing from the present invention as defined in the claims. In one such variation, the timing apparatus 80 may be adjusted so that each first sampling interval 96 occurs during the letter portion of a first response interval 85, i.e., shortly after termination of a first illumination interval 87. In this variant, each second sampling interval 98 occurs during the latter portion of a second response interval, shortly after termination of a second illumination interval 86. In this arrangement, the switching devices will sample the signals representing the response light during the gradual decay periods. Although the signals sampled still represent the intensity of the response light, the intensities prevailing during the sampling intervals will depend at least in part upon the speed of decay, i.e., on the luminescence lifetime. Therefore, this arrangement can be employed to monitor conditions which affect the luminescence lifetimes of the luminescent materials.

Figure 4:
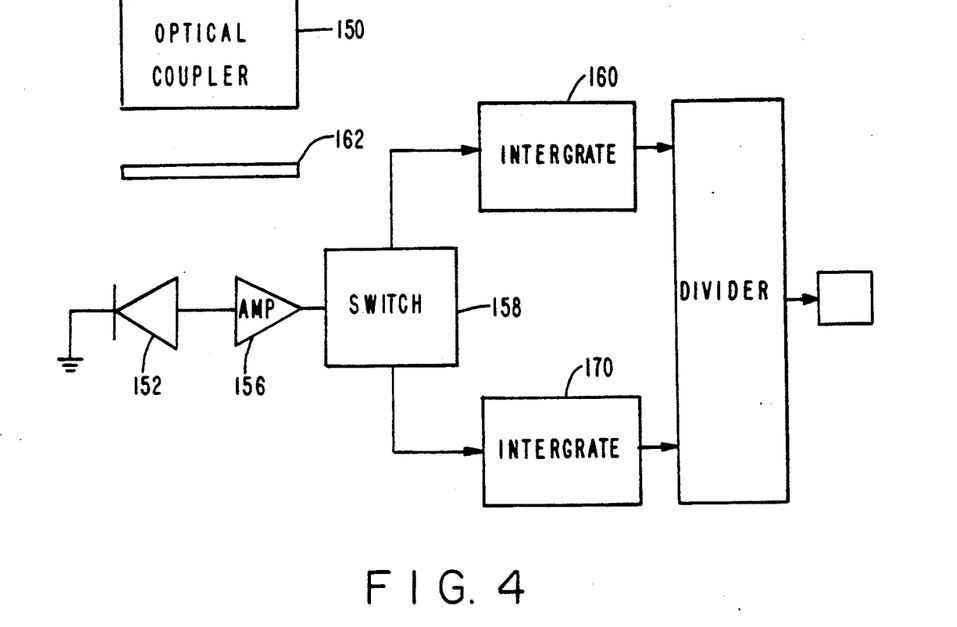
FIG. 4 is a fragmentary schematic view depicting a portion of apparatus in accordance with another embodiment of the present invention.

In a further variant, the dual photodetectors and switches depicted in FIG. 1 can be replaced by a single photodetector. The apparatus partially depicted in FIG. 4 is identical to the apparatus of FIG. 1 except that the apparatus of FIG. 4 incorporates a single photodetector 152 and a single optical band pass filter 162. Photodetector 152 and filter 162 are coupled to the probe (not shown) via an optical coupler 150, and light sources (not shown) similar to those discussed above are also coupled to the probe via coupler 150. Optical band pass filter 162 is arranged to pass light within a detector wavelength band 163 (FIG. 2) including at least some wavelengths in the response wavelength band 42 of the first luminescent material, and also including at least some wavelengths in the response wavelength band 46 of the second luminescent material. As illustrated in FIG. 2, where the response wavelength bands 42 and 46 overlap one another, the detector wavelength band may include wavelengths within the zone of overlap between these bands. Where the response wavelength bands 42 and 46 of the two luminescent materials do not overlap, the detector wavelength band may be a single, broad band encompassing portions of both response wavelength bands, or else the detector wavelength band may be a split band. Thus, filter 162 may have two relatively narrow pass bands within each of the separate response wavelength bands 42 and 46, and these narrow bands together may constitute the split pass band of the filter.

The single photodetector 152 will receive response light from both the luminescent materials. The signal is amplified by a amplifier 156, and routed to a switch 158. Switch 158 is connected to a timing device (not shown) the timing device is arranged to actuate the switch so as to connect the output of amplifier 156 to the first integrator 160 during each interval 96 (FIG. 2); to connect the output of the amplifier 156 to the second integrator 170 during each interval 98, and to disconnect the output of amplifier 156 from both integrators at other times. Thus, during each interval 96 (while the first luminescent material is emitting), the amplifier output will be connected to integrator 160. Conversely, during each interval 98 (while the second luminescent material is emitting), the amplifier output will be connected to the second integrator 170. Switch 158 thus routes a signal representing only the emissions from the first luminescent material to integrator 160, and a different signal, representing only the emissions from the second luminescent material to the second integrator 170. The divider and output circuit are the same as discussed above with reference to FIG. 1.

Apparatus according to a further embodiment of the present invention includes an illumination source 200 incorporating light sources similar to the light sources discussed above with reference to FIGS. 1-3, except that illuminator 200 incorporates devices such as a lens 202 for forming the light emitted by the light sources into a light beam 204 of substantial crosssectional area. The apparatus further incorporates a light receptor 206 which includes one or more photodetectors and optical filters such as the dual photodetectors and optical filters discussed above with reference to FIG. 1 or the single photodetector and optical filter discussed with reference to FIG. 4. Receptor 206 further includes devices such as a lens 208 for gathering light from a field of view 210 encompassing a relatively large area. The electronic components of the apparatus are similar to those discussed above. Thus, the apparatus incorporates timing devices, switches, integrators, and dividers similar to those discussed above. The apparatus of FIG. 5 further includes a probe 212 in the form of a vessel having a wall 214 formed from a transparent polymeric material such as those discussed above. A mass of luminescent composition 216 is disposed on an interior surface of wall 214. Mass 216 is in the from of a thin layer, desirably about 50 microns, and more desirably, about 10 microns thick or less. The later formed by mass 216 covers a substantial area on the surface of wall 214. Desirably, layer 216 extends over at least about 1 mm$^2$, more desirably, at least about 0.1 cm$^2$ and most desirably, at least about 0.5 cm$^2$. The layer or mass 216 incorporates first and second luminescent materials as discussed above. Illuminator 200 and receptor 206 are arranged so that the beam 204 of excitation light from the illuminator impinges on a portion of the wall 214 overlying the mass or layer 216 and passes through the transparent polymeric material of the wall so as to impinge upon a zone 218 of layer 216. Receptor 206 is arranged so that response light emitted by the luminescent material within zone 218 of layer 216 will be accepted by the photodetector or photodetectors within the receptor. The dimensions of this zone 218 are thus determined by the characteristics and arrangement of the illuminator 200 and receptor 206. Desirably, zone 218 encompasses most or all of the area of layer 216. Zone 218 thus encompasses an area of size similar to the sizes discussed above with reference to the layer itself.

Figure 5:
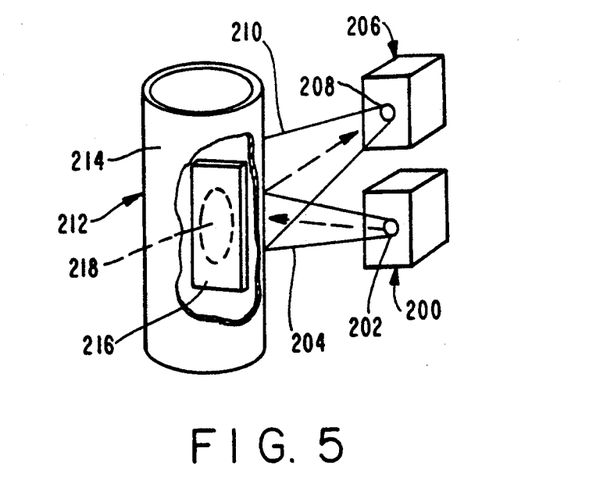
FIG. 5 is a fragmentary perspective view depicting portions of apparatus in accordance with yet another embodiment of the invention.

In operation, the timing apparatus controls the light sources within illuminator 200 to provide intervals of first and second excitation light and dwell intervals as discussed above. Likewise, the switching devices associated with the photodetector in receptor 206, the integrators and the divider are actuated in the same way as mentioned above to provide a ratiometric output signal. In this arrangement, application of excitation light to the relatively large zone 218, and detection of response light from such a large zone provides strong response light at the photodetectors. Also, the substantial response light provides strong signals which can be handled by economical, relatively low cost amplifiers and integrators without the design constraints imposed by the need to capture and amplify extremely weak signals. The photodetectors in this arrangement can be relatively insensitive, economical photodetectors, such as ordinary photodiodes, phototransistors, or the like. It is not essential to match the peak sensitivity of each photodetector in receptor 206 precisely with the peak or maximum emission wavelengths of the luminescent materials so as to obtain the maximum possible sensitivity. This ability to operate with less than maximum sensitivity is particularly useful where a single bandpass filter and/or single photodetector is employed, such as in the arrangement of components discussed above with regard to FIG. 4. Thus, the pass band of such a single filter 163 (FIG. 2) may be selected to encompass areas of overlap between the response or emission wavelength bands of the two luminescent materials even where these regions of overlap are relatively far from the peak wavelengths. Likewise, because it is not essential to obtain maximum sensitivity with the large-area luminescent layer, the wavelengths of the excitation light need not be precisely matched to the maximum absorption wavelengths of the luminescent materials. Therefore, the components of the illuminator 200 can be economical and, if necessary, relatively imprecise components. Thus, embodiments utilizing a relatively large area luminescent material mass such as the thin layer 216 are particularly suited to construction with economical components. Because the large area luminescent mass or layer provides a substantial optical signal, the signal to noise ratio is maximized. The instrument therefore can provide accurate values with little or no data averaging. Thus, the integrators utilized in the system may be operated to integrate the signal only for brief periods, rather than for many cycles of the timing apparatus. Alternatively, the integrators may be omitted entirely and replaced by devices such as analog or digital sample and hold circuitry for capturing an instantaneous value of each signal during the appropriate interval.

Thus, in an arrangement such as that illustrated in FIG. 4, switch 158 and integrators 160 and 170 can be replaced by a simple analog to digital converter for capturing and digitizing instantaneous values of the sample from amplifier 156 at appropriate times. The instantaneous value captured at a time during an interval 96 (FIG. 2) will represent the magnitude of emissions by the first luminescent material, whereas, the value captured during an interval 98 will represent the magnitude of emissions from the second luminescent material. The digital signals so derived may be supplied to a simple digital dividing circuit. Because the degree of averaging required to obtain a given degree of accuracy is reduced, the instrument using a large area luminescent layer or mass such as that depicted in FIG. 5 can provide rapid response. One particularly desirable application of this arrangement is in monitoring of oxygen concentration in biological fluid such as blood. The blood can be periodically sampled from a blood vessel via a catheter and placed in a vessel such as that illustrated in FIG. 5. Alternatively, vessel 212 may be configured as part of a continuous flow system as, for example, the extracorporeal blood flow circuit of a mechanical blood pump and oxygenator. A dialysis machine or the like, so that blood flows continuously through the vessel.

The following non-limiting examples illustrate certain features of the invention:

EXAMPLE I 7.3 mg Platinum 2,3,7,8,12,13,17,18 Octaethyl 21H,23H Porphine ("Pt-OEP") and 1.00 g Dimethylsiloxanebis-phenol A block copolymer of the type sold under the designation PS099 by the Petrarch company of Bristol, Pa. were dissolved in tetrahydrofuran ("THF"). This solution was deposited on a substrate and the THF was evaporated to leave a film of 10 millimolar Pt-OEP in PS099.

The film exhibits an absorption band with a peak or maximal absorption at 535 nm. Upon excitation by 535 nm light, the film emits response light in a response wavelength band centered on the peak response or peak emission wavelength at 646 nm. The film is excited at 535 nm and the emission intensity at 646 nm is monitored while exposing the film to different gases. The emission intensity (in arbitrary units) is 92 while the film is exposed to substantially pure nitrogen; 32 while the film is exposed to ambient air; and 18 while the film is exposed to substantially pure oxygen, thus demonstrating modulation of the emission intensity by oxygen concentration.

EXAMPLE II

The procedures of Example I were repeated, but with different amounts of Pt-OEP to yield differing concentrations of Pt-OEP in the PS-099 polymer film. The response is measured only in substantially pure nitrogen and in ambient air. The results are as follows:

| Pt-OEP Concentration (millimolar) | Emission Intensity (arbitrary units) | |
| --- | --- | --- |
| In PS099 | In Nitrogen | In Air |
| 1.0 | 90.0 | 29.0 |
| 2.5 | 90.0 | 29.2 |
| 5.0 | 90.0 | 30.9 |
| 10.0 | 90.0 | 32.8 |
| 20.0 | 90.0 | 49.8 |

EXAMPLE III

The procedures of Example II are repeated, except that a dimethylsiloxane-alphamethylstyrene block copolymer of the type sold under the designation PS096.5 by the Petrarch Company is employed instead of PS099. The results are as follows:

| Pt-OEP Concentration (millimolar) | Emission Intensity (arbitrary units) | |
| --- | --- | --- |
| In PS096.5 | In Nitrogen | In Air |
| 1.0 | 90.0 | 22.1 |
| 2.5 | 90.0 | 22.1 |
| 5.0 | 90.0 | 21.9 |
| 10.0 | 90.0 | 23.0 |
| 20.0 | 90.0 | 23.6 |

These results indicate greater sensitivity of emission intensity to oxygen concentration than with the PS099 polymer of Examples I and II. These results are consistent with the greater solubility of oxygen in PS096 than in PS099.

EXAMPLE IV

A film containing 5.0 millimolar Pt-OEP and 5.0 millimolar 2, 3, 7, 8, 12, 13, 17, 18, octaethyl 21H-23H porphine ("$H_2$-OEP") in PS099 polymer is prepared by procedures as in Example I. As in Example I, Pt-OEP has an absorption peak at about 535 nm and emission at 640-700 nm. $H_2$-OEP exhibits an absorption peak at 622 nm and emission at about 670-700 nm. The emission intensity of the individual luminescent materials is monitored by alternately exciting the film with light at 535 nm (Pt-OEP absorption band) and monitoring the resulting emission intensity at 676 nm then applying excitation light at 622 nm ($H_2$-OEP absorption) and monitoring the resulting emission intensity. This monitoring is repeated in air and in nitrogen. The results are as follows:

| Gas | Pt-OEP Emission Intensity | $H_2$-OEP Emission Intensity | Ratio of $H_2$-OEP Emission Intensity To Pt-OEP Emission Intensity |
| --- | --- | --- | --- |
| Air | 38 | 87 | 2.29 |
| Nitrogen | 92 | 91 | 0.99 |

These results show that the emission intensity of $H_2$-OEP is far less sensitive to oxygen concentration than the emission intensity of Pt-OEP. Accordingly, the ratio of emission intensities changes with oxygen concentration in the environment. This ratio serves as a measure of oxygen content in the environment.

EXAMPLE V

The procedure of Example IV is repeated using 2, 3, 7, 8, 12, 13, 17, 18 octoethyl 21H, 23H porphine ruthenium (II) carbonyl, 1:1 complex (hereinafter "Ru-OEP") instead of the $H_2$-OEP used in Example IV. Ru-OEP absorbs light at 568 nm and has an emission peak at about 622 nm. The emission intensity of Ru-OEP is substantially the same when the film is in ambient air as when the film is in nitrogen. The Ru-OEP emission intensity is substantially unaffected by oxygen concentration.

EXAMPLE VI

The procedure of Example V is repeated except that zinc 2, 3, 7, 8, 12, 13, 17, 18 octoethyl 21H, 23H porphine (hereinafter "Zn-OEP") is employed in place of Ru-OEP or $H_2$-OEP. Zn-OEP has an absorption peak at 567 nm and an emission peak at about 625 nm. The Zn-OEP emission intensity is not substantially affected by oxygen concentration.

EXAMPLE VII

A film containing 4.1 mg platinum 5, 10, 15, 20 tetraphenyl 21H, 23H porphine ("Pt-TPP"), 16.2 mg, 5, 10, 15, 20 tetraphenyl 21H, 23H porphine Ruthenium (II) carbonyl ("Ru-TPP"), 1:1 complex with THF and 1.00 g PS099 is prepared by a solvent casting procedure as discussed above in Example I. Pt-TPP absorbs at 510 nm and emits at about 658 nm. Ru-TPP absorbs at about 598 nm and emits at about 658 nm. The emission of response wavelength bands of Ru-TPP and Pt-TPP substantially overlap one another, but the two luminescent materials in the film can be selectively excited by applying excitation light either at about 510 nm or at about 598 nm. In pure nitrogen, the emission intensity of Pt-TPP in this film is about 95, whereas, the emission intensity of Ru-TPP is about 27, so that the ratio of Ru-TPP intensity to Pt-TPP intensity is about 0.28. In air, the emission intensity of Pt-TPP is about 47.5 whereas, the emission intensity of Ru-TPP is about 24, so that the ratio of Ru-TPP intensity to Pt-TPP intensity is about 0.51. Stated another way, Ru-TPP and Pt-TPP have differing sensitivities to oxygen and hence the ratio of emission intensities from these two luminescent materials is a measure of oxygen concentration.

EXAMPLE VII

The procedure of Example IV is repeated using palladium 2,3,7,8,12,13,17,18 octaethyl 21H, 23H porphine (hereinafter "pd-OEP") and 2,3,7,8,12,13,17,18 octoethyl porphine ("$H_2$-OEP"). Pd-OEP exhibits an absorption band at about 544 nm and an emission or response band at about 663 nm. $H_2$-OEP has an absorption band at about 621 nm and an emission or response band at about 689 nm. The emission intensities from Pd-OEP and from $H_2$-OEP are monitored by alternately exciting the two materials while exposing the film to pure nitrogen, air and pure oxygen, with the results shown below:

| Gas | Pd-OEP Emission Intensity | $H_2$-OEP Emission Intensity | Ratio of $H_2$-OEP Emission Intensity To Pd-OEP Emission Intensity |
| --- | --- | --- | --- |
| Nitrogen | 91.5 | 91.2 | 0.99 |
| Air | 28.7 | 90.0 | 3.14 |
| Oxygen | 7.3 | 81.2 | 11.12 |

In this example, the palladium derivative gives similar results to the platinum derivative of Examples III and IV.

Numerous further variations and combinations of the features discussed above can be utilized without departing from the invention as defined by the claims. Accordingly, the foregoing description of the preferred embodiment should be taken by way of illustration rather than by way of limitation of the invention as claimed.

What is claimed is:

1. Apparatus for monitoring a condition comprising:
   (a) a probe including a first luminescent material which absorbs light within a first band of absorption wavelengths and temporarily emits light in response to such absorption, and a second luminescent material which absorbs light in a second band of absorption wavelengths and temporarily emits light in response to the absorption in said second band, at least a portion of said second absorption band being outside of said first absorption band, said luminescent materials having different sensitivities to the condition to be monitored;
   (b) means for applying first excitation light at one or more wavelengths within said first absorption band but outside of said second absorption band and second excitation light at one or more wavelengths within said second absorption band but outside of said first absorption band to said luminescent materials in said probe alternately, in alternating first and second illumination intervals whereby said luminescent materials in said probe will emit response light in an alternating sequence including first response intervals of emission by said first luminescent material and second response intervals of emission by said second luminescent material;
   (c) means for detecting response light emitted by said luminescent materials and providing a first signal representing the magnitude of said response light during said first response intervals, and a second signal representing the magnitude of said response light during said second response intervals, whereby said first and second signals will represent the intensity of emission of said first and second luminescent materials respectively; and
   (d) means responsive to said first and second signals for determining a quantitative relationship between said intensities as represented by said first and second signals, whereby said quantitative relationship will vary in accordance with the condition to be monitored.

2. Apparatus as claimed in claim 1 wherein said first and second luminescent materials are such that said first and second absorption bands lie substantially within the range of visible light wavelengths, and wherein said first and second luminescent materials are materials which emit said response light at visible wavelengths.

3. Apparatus as claimed in claim 2 wherein said probe includes a polymeric member substantially transparent to light in said first and second absorption bands and to said response light, said means for applying excitation light including means for directing said excitation light to said luminescent materials of said probe through said polymeric member, said means for detecting light including means for detecting response light transmitted through said polymeric member.

4. Apparatus as claimed in claim 3 wherein said polymeric member is a fiber having proximal and distal ends, said luminescent materials being disposed at said distal end of said fiber.

5. Apparatus as claimed in claim 1 wherein said probe includes a member having a wall and said luminescent materials are disposed in one or more layers on said wall of said member.

6. Apparatus as claimed in claim 5 wherein each said layer extends over a portion of said wall surface encompassing an area of at least about 1 $mm^2$, said means for applying excitation light including means for applying said excitation light to a zone of each said layer encompassing at least about 1 $mm^2$.

7. Apparatus as claimed in claim 6 wherein said member is a wall of a vessel.

8. Apparatus as claimed in claim 6 wherein said means for detecting said response light includes one or more semiconductor elements having electrical characteristics which vary in response to light impinging upon the semiconductor element, and means for directing said response light onto said one or more semiconductor elements.

9. Apparatus as claimed in claim 8 wherein said first and second luminescent materials are materials which emit said first and second response light in first and second response wavelength bands, respectively, said first and second response wavelength bands overlapping one another.

10. Apparatus as claimed in claim 1 wherein said means for detecting said response light and providing said first and second signals includes means for detecting light in a detector band of wavelengths encompassing at least some wavelengths common to said first and second response light bands.

11. Apparatus as claimed in claim 10 wherein said means for detecting said response light and providing said first and second signals includes a single photodetector for detecting light in said detector wavelength band and providing a photodetector signal representing such detected light and means for deriving said first signal from said photodetector signal prevailing during said first response intervals and deriving said second signal from said photodetector signal prevailing during said second response intervals.

12. Apparatus as claimed in claim 1 wherein said means for applying excitation light is operative to provide a dwell period after each illumination interval and wherein said luminescent materials are phosphorescent, whereby said response intervals extend into said dwell periods, said means for detecting said response light being operative to detect said response light during portions of said first and second response intervals within said dwell periods, whereby the intensities of response light represented by said signals will depend at least in part upon the emission lifetimes of said luminescent materials.

13. Apparatus as claimed in claim 1 wherein said luminescent materials are materials which emit said response light during said illumination intervals, whereby at least a portion of each said response interval overlaps one of said illumination intervals, said means for detecting said response light being operative to detect said response light during portions of said response intervals which overlap said illumination intervals.

14. Apparatus as claimed in claim 1 wherein said first and second luminescent materials are such that said intensity of emission of said first luminescent material varies in response to the condition to be monitored and said intensity of emission of said second luminescent material is substantially insensitive to the condition to be monitored.

15. Apparatus as claimed in claim 1 wherein said first and second luminescent materials have substantially equal susceptibility to loss of emission intensity upon exposure to said excitation light.

16. Apparatus as claimed in claim 1 wherein said means for determining a quantitative relationship includes means for determining a ratio between said intensities as represented by said signals.

17. Apparatus as claimed in claim 1 wherein each of said luminescent materials includes a compound selected from the group consisting of porphyrin, chlorin, bacteriochlorin, isobacteriochlorin, porphyrinogen and derivatives thereof.

18. Apparatus as claimed in claim 17 wherein said first luminescent material includes a metallic moiety selected from the group consisting of platinum and palladium and said second luminescent material is substantially free of platinum and palladium.

19. Apparatus as claimed in claim 1 wherein said luminescent materials are selected from the group consisting of:

(1) compounds according to the formulae:

porphyrin chlorin bacteriochlorin isobacteriochlorin porphyrinogen porphyrin chlorin bacteriochlorin isobacteriochlorin porphyrinogen where $R_1$ through $R_{12}$ are the same or different and are selected from the group consisting of hydrogen, substituted and unsubstituted aryl moieties, and substituted and unsubstituted alkyl moieties, (2) metallo derivatives of said compounds; and
(3) combinations of said compounds; and
(4) combinations of said metallo derivatives.

20. Apparatus for monitoring a condition comprising:
(a) first and second luminescent materials selected from the group consisting of:
  (1) compounds according to the formulae:

wherein $R_1$ through $R_{12}$ are the same or different and are selected from the group consisting of hydrogen, substituted and unsubstituted alkyl moieties and substituted and unsubstituted aryl moieties;
  (2) metallo derivatives of said compounds;
  (3) combinations of said compounds; and
  (4) combinations of said metallo derivatives;
said first and second luminescent materials having different sensitivities to the condition to be monitored;
(b) means for exposing said luminescent materials to the condition to be monitored;
(c) means for applying excitation light to said luminescent materials, whereby said luminescent materials will emit a first response light from said first luminescent material and second response light from said second luminescent material;
(d) means for detecting said first and second response light and providing a first signal representing the intensity of the first response light from said first luminescent material and a second signal representing the intensity of the second response light from said second luminescent material; and
(e) means responsive to said signals for determining a relationship between said intensities (e), line 2 are represented by said first and second signals, whereby said quantitative relationship will vary in accordance with the condition to be monitored.

21. Apparatus as claimed in claim 20 wherein said first luminescent material is selected from the group consisting of platinum derivatives of said compounds, palladium derivatives of said compounds and combinations thereof, and wherein said second luminescent material is selected from the group consisting of said compounds, metallo derivatives of said compounds other than platinum and palladium derivatives, and combinations thereof.

22. Apparatus as claimed in claim 20 further comprising a polymeric light-transmissive member, said means for applying excitation light including mans for directing said excitation light through said polymeric member, said means for detecting response light including means for detecting response light transmitted through said polymeric member.

23. Apparatus as claimed in claim 21 wherein said polymeric member is a fiber optic.

* * * * *